United States Patent [19]

Wachs

[11] Patent Number: 5,907,066

[45] Date of Patent: May 25, 1999

[54] TREATING METHANOL-CONTAINING WASTE GAS STREAMS

[75] Inventor: Israel E. Wachs, Bridgewater, N.J.

[73] Assignee: Lehigh University, Bethlehem, Pa.

[21] Appl. No.: 08/943,217

[22] Filed: Oct. 6, 1997

Related U.S. Application Data

[60] Provisional application No. 60/031,950, Nov. 27, 1996.

[51] Int. Cl.⁶ .................................................. C07C 45/00
[52] U.S. Cl. ......................... 568/472; 568/449; 502/350; 585/638; 585/640; 423/415.1; 423/512.1; 162/16
[58] Field of Search .................................... 585/638, 640, 585/639; 502/350, 353; 568/449, 472, 474; 423/415.1, 512.1; 162/14, 16

[56] References Cited

U.S. PATENT DOCUMENTS

| | | |
|---|---|---|
| 4,544,649 | 10/1985 | Wachs et al. . |
| 4,814,541 | 3/1989 | Lewis . |
| 4,861,938 | 8/1989 | Lewis et al. . |
| 4,873,390 | 10/1989 | Lewis et al. . |
| 4,973,972 | 11/1990 | Lewis et al. . |
| 5,157,181 | 10/1992 | Stine et al. . |
| 5,176,897 | 1/1993 | Lester . |
| 5,292,704 | 3/1994 | Lester . |

FOREIGN PATENT DOCUMENTS

| | | |
|---|---|---|
| 0 068 377 | 1/1983 | European Pat. Off. . |
| 0 267 711 | 5/1988 | European Pat. Off. . |
| 212993 | 1/1967 | Russian Federation . |
| 8 002 177 | 9/1981 | Sweden . |
| 1263139 | 2/1972 | United Kingdom . |
| 2238486 | 6/1991 | United Kingdom . |

OTHER PUBLICATIONS

International Searh Report for PCT/US97/20968 dated Apr. 27, 1998 (Abstract only).
Garner, "Methanol Emission Control Options Meet EPA 'Cluster' Requirements," Pulp and Paper, Aug. 1996, 59–62.
Jehng, et al., "Surface Modified Niobium Oxide Catalyst: Synthesis, Characterization, and Catalysis," Applied Catalysis A, vol. 83, 179–200, 1992.
Kim and Wachs, "Surface Chemistry of Supported Chromium Oxide Catalysts," Journal of Catalysis, vol. 142, 166–171, 1993.
Jehng and Wachs, "Molecular Design of Supported Niobium Oxide Catalysts," Catalysis Today, vol. 16, 417–426, 1993.
Kim and Wachs, "Surface Rhenium Oxide–Support Interaction for Supported $Re_2O_7$ Catalysts," Journal of Catalysis, vol. 141, 419–429, 1993.
Deo, et al., "Physical and Chemical Characterization of Surface Vanadium Oxide Supported on Titania: Influence of Titanaia Phase (Antase, Rutile, Brookite and B)," Applied Catalysts A, vol. 91, 27–42, 1992.
Deo and Wachs, "Reactivity of Supported Vanadium Oxide Catalysts: The Partial Oxidation of Methanol," Journal of Catalysis, vol. 146, 323–334, 1994.

Deo and Wachs, "Effect of Additives on the Structure and Reactivity of the Surface Vanaduim Oxide Phase in $V_2O_5$/$TiO_2$ Catalysts," Journal of Catalysis, vol. 146, 335–345, 1994.
Jehng, et al., "Surface Chemistry of Silica–Titania–Supported Chromuim Oxide Catalysts," J. Chem. Soc. Faraday Trans., vol. 91(5), 953–961, 1995.
Kim, et al., "Molecular Structures and Reactivity of Supported Molybdenum Oxide Catalysts," Journal of Catalysis. vol. 146, 268–277, 1994.
Banares, et al., "Molybdena on Silica Catalysts: Role of Preparation Methods of the Structure–Selectivity Properties for the Oxidation of Methanol," Journal of Catalysis, vol. 150, 407–420, 1994.
Jehng and Wachs, "The Molecular Structures and Reactivity of $V_2O_5$/$TiO_2$/$SiO_2$ Catalysts," Catalyst Letters, vol. 13, Sep. 20, 1992.
Yang and Kung, "Hydrogen Recovery From Hydrogen Sulfide By Oxidation and By Decomposition," Ind. Eng. Chem. Res., vol. 33, 1090–1097, 1994.
Mehta, "Unbleached Mills Won't Escape Impact of EPA's 'Cluster Rules'," Pulp and Paper, 71–70, 1995.
Furguson, "Odor Control: Location, Process Determines Nuisance Level," Pulp and Paper, 147–148, 1995.
Nichols, "EPA's Proposed Cluster Rules Shape U.S. Paper Industry's Near Future," Pulp and Paper, 75–85, Sep. 1994.
Sazonova, et al., "Relationship Between Sulfur Dioxide Oxidation and Selective Catalytic No Reduction By Amonia On $V_2O_5$–$TiO_2$ Catalysts Doped With $WO_3$ and $Nb_2O_5$," React. Kinet. Catal. Lett., vol. 52, No. 1, 101–106, 1994.
Bosch and Janssen, "Catalytic Reduction of Nitrogen Oxides," Catalysis Today, vol. 2, No. 4, 379, 381–382, 1988.
Weigand and Friend. "Model Studies of the Desulfurization Reactions on Metal Surfaces and in Organometallic Complexes," Chemical Reviews, vol. 92, No. 4, 494–504, 1992.
Busca, et al., "Mechanism of Selective Methanol Oxidation Over Vanadium Oxide–Titanium Oxide Catalysts: A FT–IR and Flow Reactor Study," J. Phys. Chem., vol. 91, 5263–5269, 1987.
"Formation and Control of Nitrogen Oxides," Catalysis Today, vol. 2, 369–379, 1988.
Weigand, et al., "The Local Structure of Absorbed methyl Thiolate: The Reactions of Methanethiol on Mo(110)," Surface Science, vol. 279, 105–112, 1992.

(List continued on next page.)

*Primary Examiner*—Shailendra Kumar
*Assistant Examiner*—Screeni Pad Manabhan
*Attorney, Agent, or Firm*—Banner & Witcoff, Ltd.

[57] ABSTRACT

A method wherein a methanol-containing waste gas stream, such as a pulp mill waste stream which contains methanol and other waste products, including methyl mercaptans, is passed in contact with a catalyst comprising certain supported metal oxides in the presence of an oxidizing agent; preferably the gas stream is contacted with the catalyst, in the presence of the oxidizing agent, for a time sufficient to convert at least a portion of the methanol to formaldehyde ($CH_2O$).

21 Claims, 12 Drawing Sheets

OTHER PUBLICATIONS

Bol and Friend, "The Effects of Oxygen on Selectivity: The Reactions of 2–Propanethiolate on Oxygen–Covered Rh(111)," vol. 117, 5351–5358, 1995 (J. Amer. Chem. Soc.).

Turk, et al., "Ammonia Injection Enhances Capacity of Activated Carbon for Hydrogen Sulfide and Methyl Mercaptan," Enviro. Sci. Technol., vol. 23, No. 10, 1242–1245, 1989.

TREATING METHANOL-CONTAINING WASTE GAS STREAMS

This application claims the priority benefits from the U.S. provisional application Ser. No. 60/031,950, filed Nov. 27, 1996.

BACKGROUND OF THE INVENTION

1. Field of the Invention

This invention broadly relates to a process for treating methanol-containing waste gas streams, such as encountered in a paper (pulp) mill. More particularly, this invention provides a method wherein a gas stream, such as from a paper pulp mill containing methanol, and other waste products, including methyl mercaptans, is passed in contact with a catalyst comprising certain supported metal oxides in the presence of an oxidizing agent. In a preferred embodiment, the gas stream is contacted with the catalyst, in the presence of the oxidizing agent, for a time sufficient to convert at least a portion of the methanol to formaldehyde ($CH_2O$).

2. Description of Related Art

Pulp mills that chemically digest wood sources, such as by using the Kraft process, generate a significant amount of by-product methanol, in addition to other potential pollutants such as reduced sulfur compounds, higher alcohols, terpenes, acetone, amines, acetaldehyde and methyl ethyl ketone. Significant methanol emissions are encountered during the overall pulping and paper-making operation, particularly from the following pulp mill sub-systems: pulp digesters, blow heat recovery units, and multiple-effect evaporators. In the past, this methanol was often discharged into the air or directly into wastewater. With growing environmental concerns over pollution caused by these past practices, however, more stringent emission requirements have evolved. As a consequence, processes must be developed to dispose of the methanol, and the other pulp mill by-products, in a more environmentally satisfactory manner. At the present time, two alternatives have been suggested as being suitable for complying with regulatory standards. Gamer, Jerry, *Pulp & Paper*, (Aug. 1996):59–62. In both approaches, the various waste steams generated in a pulp mlll containing by-product methanol, and a variety of the other noted compounds, are first consolidated into a single condensate stream.

In a first alternative, this consolidated condensate stream is fed to a steam stripping column which is operated in a way to remove and concentrate, in the gas phase, a major portion of the pollutants from the liquid condensate. Over 80–90% of the methanol of the consolidated feed steam is removed in the stripping column, while the methanol concentration is increased from about 0.1–0.5% in the liquid feed to about 35–55% in the steam stripper gaseous overhead.

This methanol-containing stripper overhead is then treated by indiscriminate (noncatalytic) oxidation (incineration) to produce a waste gas that can be safely discharged into the environment. To safely complete the oxidation of the gas constituents, the incineration process must be operated at temperatures approaching 1000° C. Such operation generally requires the use of an auxiliary fuel source. In some facilities, the fuel value of the stripper overhead is recovered by using it, for example, to power a boiler or a lime kiln. In some cases, the methanol content of the stripper overhead is further concentrated by distillation to increase its value before use as a fuel.

The second alternative delivers the condensate stream to a wastewater treatment system where aerobic microorganisms use the methanol as a carbon source, converting it to carbon dioxide and water.

While highly dependent on the wood source and the basic operating conditions of a pulp mill, the consolidated waste methanol stream or condensate from a pulp mill can be expected to contain, among other materials, methanol and other higher alcohols, methyl ethyl ketone, acetaldehyde, acetone, terpenes, amines, ammonia and reduced sulfur compounds. The concentration of these materials in the aqueous condensate is enriched by steam stripping and results in a gas stream which typically contains about 40–55 wt. % methanol, 2–8 wt. % higher alcohols, such as ethanol and isopropanol, 2–8 wt. % ketones, including methyl ethyl ketone, methyl isobutyl ketone and acetone, 1–3 wt. % reduced sulfur compounds including hydrogen sulfide and methyl mercaptans, such as methanethiol ($CH_3SH$), dimethyl sulfide ($CH_3SCH_3$) and dimethyl disulfide ($CH_3SSCH_3$) about 1–2 wt. % amines, including ammonia, 1–6 wt. % terpenes, such as α-pinene and α-terpineol, and the balance (generally 40–50 wt. %) water.

Simply incinerating or biologically degrading this methanol-containing waste stream constitutes a costly and inefficient use of the inherent resources present in the stream. While procedures used to recover the fuel value of the stream seek to reduce such inefficiencies, they create their own source of problems. In particular, the variable nature of the methanol-containing stream creates the risk of operational upsets in the operation of the lime kiln or a boiler. Further, if the lime kiln or boiler operation is interrupted, then the operation of the stripper must be discontinued since there is no way to dispose the concentrated stripper overhead. As a result of these potential problems, a pulp mill likely would need to operate with a dedicated incinerator using a power boiler as back-up.

In its preferred aspects, the present invention is directed to an improved process for using by-product methanol from methanol-containing waste streams, such as encountered in a paper (pulp) mill, to produce a valuable chemical commodity, formaldehyde.

BRIEF DESCRIPTION OF THE INVENTION

Figure 1:
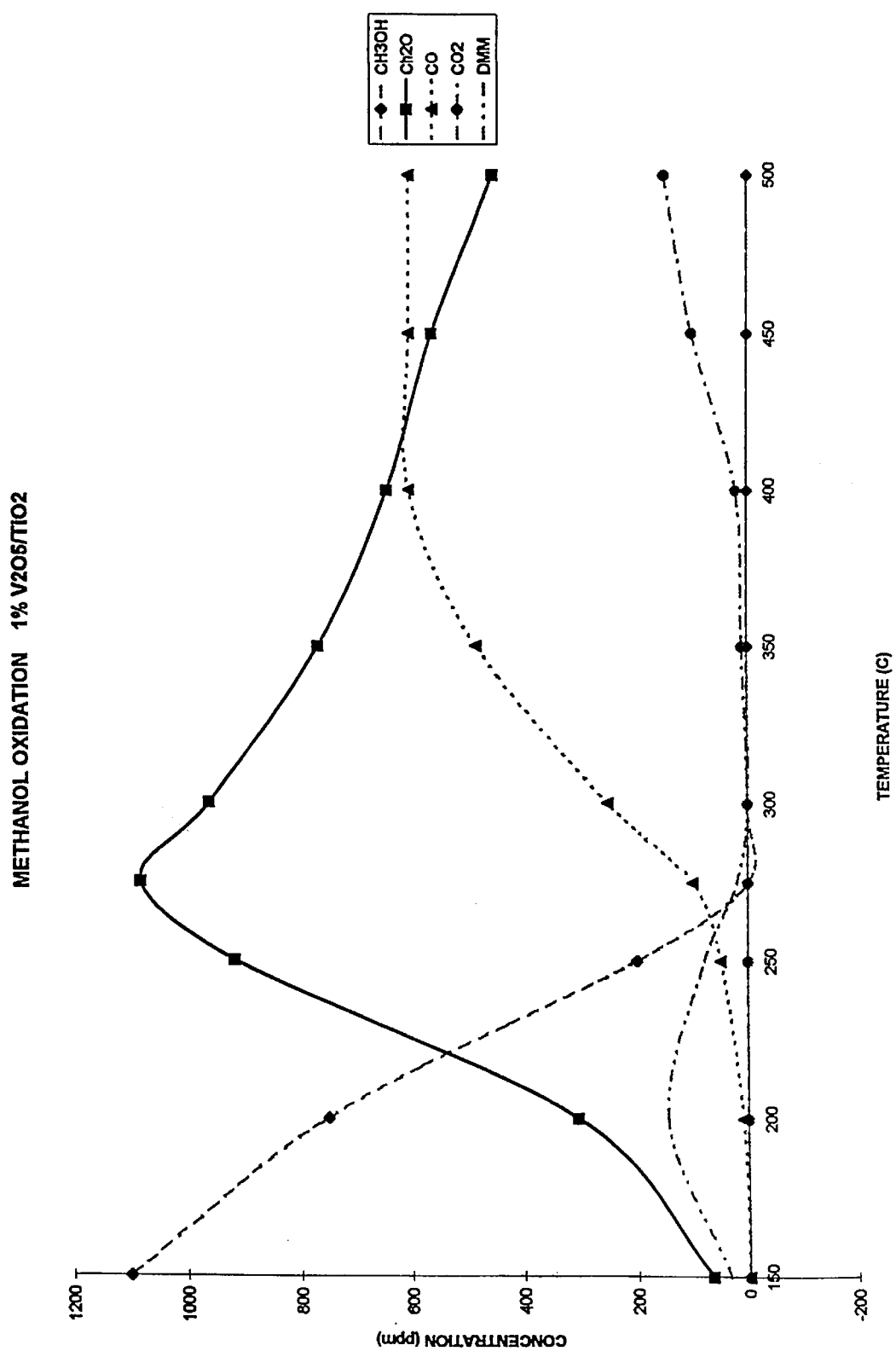
FIG. 1 illustrates the distribution of products (reactor exit gas concentration in ppm) produced by oxidizing methanol over a vanadia on titania catalyst containing about 1% by weight vanadia over the temperature range of 150° to 450° C.

This invention provides a method wherein a methanol-containing waste gas stream, such as originates from a paper pulp mill, and containing other waste products, including methyl mercaptans, is contacted, under oxidizing conditions, with a catalyst comprising a supported metal oxide. The gas is preferably passed in contact with the catalyst in the presence of the oxidizing agent for a time sufficient to convert at least a portion of the methanol to formaldehyde ($CH_2O$), and then recovering the formaldehyde as a product stream separate from the gas stream. In an alternative embodiment, the gas can be contacted with the catalyst for a time sufficient, and under oxidizing conditions sufficient, to oxidize the carbon-containing oxidizable components of the gas stream, including methanol, completely to carbon oxides ($CO_x$) and the sulfur-containing components to sulfur oxides ($SO_x$).

The oxidizing conditions can be established using an oxidizing agent such as oxygen or air. In the presence of the catalyst, other volatile organic compounds beside methanol are also oxidized, amines are generally reduced to nitrogen (though some portion may be oxidized to nitrogen oxides) and the sulfur is oxidized to $SO_2$, and possibly a minor amount of $SO_3$.

Accordingly, a preferred embodiment of the present invention is directed to a process for producing formaldehyde from methanol-containing waste gas streams, especially pulp mill condensates, which comprises (1) producing a methanol-containing gas from the condensate, such as by steam stripping the pulp mill condensates, (2) contacting said methanol-containing waste gas with a supported metal oxide catalyst under oxidizing conditions for a time sufficient to convert at least a portion of the methanol to formaldehyde, and (3) recovering said formaldehyde from the gas stream. Following removal of the formaldehyde, the residual gas stream likely will be sent to an incinerator or after-burner for complete combustion of the residual impurities and products so as to produce a gas suitable for direct discharge into the atmosphere.

In carrying out the process of the present invention, the metal oxide overlayer of the supported metal oxide is typically based on a metal selected from the group consisting of titanium (Ti), zirconium (Zr), molybdenum (Mo), rhenium (Re), vanadium (V), chromium (Cr), tungsten (W), manganese (Mn), niobium Nb), tantalum (Ta) and mixtures thereof and the support generally is selected from titania, silica, zirconia, alumina, ceria, magnesia, niobia, lanthanum oxide, tin oxide and mixtures thereof. As a general rule, titanium (Ti), zirconium (Zr), niobium (Nb), tantalum (Ta) and tungsten (W) should not be used as the sole catalytic species with a silica support and the support and the supported metal should not be identical.

The supported metal oxide catalyst compositions useful for practicing the present invention are known in the prior art.

DETAILED DESCRIPTION OF THE INVENTION

In accordance with the present invention, a methanol-containing waste gas stream, such as a pulp mill waste gas stream containing methanol, and containing a variety of other components including higher alcohols, methyl ethyl ketone, methyl isobutyl ketone, acetaldehyde, acetone, terpenes, amines, ammonia and reduced sulfur compounds, is treated by contacting the waste gas stream, under an oxidizing condition, with a supported metal oxide catalyst. Such a gas can be obtained from a kraft pulp mill by steam stripping the condensate stream consolidated from a variety of pulp mill processing steps. Depending upon the contacting conditions, such as the nature of the catalyst, the temperature, the catalyst loading and the like, the constituents of the waste gas stream may be partially or completely oxidized. Preferably, the conditions are selected to facilitate partial oxidation of at least the methanol in the stream to formaldehyde. Importantly, the partial oxidation of methanol to formaldehyde using the catalysts of the present invention is not adversely affected by the presence of a large amount of water, which typically comprises 40–50 wt. % of the gas stream, a significant amount of reduced sulfur compounds, such as hydrogen sulfide and methyl mercaptans, and amines, found in the pulp mill condensates. It has been observed that the methanol is oxidized selectively to formaldehyde in the presence of this large amount of water and reduced sulfur compounds.

In accordance with the present invention, the waste gas stream containing the methanol and other oxidizable carbon and sulfur-based constituents contacts the supported metal oxide catalyst under oxidizing conditions at a temperature in the range of 200° to 700° C., preferably in the range of 300° to 600° C. and most often in the range of 325° to 500° C. The oxidizing agent can usually be oxygen or air. In the preferred approach, the contacting of the methanol-containing pulp mill waste gas with the supported metal oxide catalyst under an oxidizing atmosphere, e.g., in the presence of oxygen, and at an appropriate temperature, causes a selective conversion of the methanol to formaldehyde. The oxidizable constituents of the gaseous feed stream generally will comprise at least about 0.1 mole %, and preferably at least 1.0 mole % and higher of methanol, although higher concentrations may be employed. The gas stream will also include many other oxidizable or inert constituents. For illustrative purposes only, for example, other oxidizable components of the gas stream may include hydrogen sulfide, methyl mercaptans, terpenes, acetone, methyl ethyl ketone, amines and higher alcohols. The gas stream may also include water. The gas stream preferably contacts the catalyst at a temperature of about 325° to 450° C.

The waste gas or any of its precursor streams, e.g., the consolidated pulp mill condensate, may be treated to reduce the concentration of constituents that may cause fouling of the catalytic or catalyst support surface. For example, higher concentration of terpenes, e.g., concentrations above 500–1000 ppm, have demonstrated a tendency to cause carbon deposition on the catalyst or catalyst support surface depending on the severity of the pulp mill concentrate vaporization conditions. This carbon can be easily burned off (removed by oxidation from) the catalyst and its support to restore its catalytic activity. However, to avoid frequent interruptions in the operation of the catalytic reactor for regenerating the catalyst, it may be preferred in some applications to reduce the concentration of such carbon-forming constituents below such concentrations.

To achieve high selectivity in the conversion of methanol, contained for example in a pulp mill waste gas stream, to formaldehyde, it is important to maintain the flow rate of the gas stream to provide an amount of methanol per unit mass of catalyst in the range of $10^{-2}$ to $10^5$ cubic centimeters of methanol (assessed under standard conditions of temperature and pressure (STP)) per gram of active catalyst per minute (excluding inert ceramic components or other inert catalyst support material). Given the typical composition of the pulp mill waste gas, such conditions will also facilitate proper oxidation of the other components of the gas stream as well. Generally, higher reaction temperatures permit higher flow rates. Usually, the process can be operated at 0.1 to $10^4$, cubic centimeters (STP) of methanol per gram of catalyst per minute.

As used herein, the term "selectively" is intended to embrace the conversion of at least 1% of the methanol, preferably at least 10% of the methanol, more usually at least 50% of the methanol and most often at least 70%, and most preferably 95% of the methanol which contacts the catalyst, to formaldehyde. Selectivity, as that term is used herein, is determined by dividing the moles of formaldehyde in the methanol conversion products by the moles of methanol converted (consumed) from the feed to the reactor.

The oxidation reaction is exothermic. As recognized by those skilled in the art, a variety of reactor designs maybe employed to accommodate the necessary mass and heat transfer processes for effective operation of the process on a continuous basis. The reaction may be conducted at atmosphere pressure and above, or below atmospheric pressure.

Formaldehyde is the intended product and it can be recovered from the gaseous reaction products using any one of a number of ways known to those skilled in the art.

As will be recognized by those skilled in the art, the gases leaving the reactor may contain unreacted starting products, including inert gases that may have been added, as well as formaldehyde and water. The principal by-product that is formed during the partial oxidation of methanol is carbon monoxide, which may be accompanied by a small amount of carbon dioxide. Oxidation of the other usual constituents in the pulp mill waste gas stream also leads to carbon oxides, as well as sulfur oxides and possibly additional formaldehyde. COS may also be a minor product.

The reaction mixture leaving the catalytic reactor is generally subject to further processing in a conventional manner. For example, the formaldehyde product can be separated in a washer (absorber), or by indirect cooling, or also by fractional cooling. For example, the washing can be performed with water, in which case a multi-stage washer can be used. An aqueous formaldehyde solution is obtained in this manner. From this solution commercial formaldehyde solutions can be prepared by distillation for immediate technical use. The formaldehyde also can be condensed out of the reaction gas together with the water that has formed. In this manner, concentrated formaldehyde solutions in common commercial form eventually can be obtained. Other ways for isolating and recovering the formaldehyde product will be apparent to those skilled in this art.

The residual gas stream, following removal of formaldehyde, can be treated in an incinerator, to combust (fully oxidize) any residual oxidizable constituents, before discharging the gas stream into the atmosphere. Alternatively, if the residual gas contains a significant amount of methanol, the gas stream can be recycled for additional treatment in the catalytic reactor.

For obtaining higher yields and selectivities in the conversion of the methanol contained in the pulp mill waste gas to formaldehyde, it may be desirable to conduct the reaction such that only a partial reaction takes place in a single pass through the reactor. For example, the pressure, temperature, composition of the starting gas mixture, the amount of catalyst and/or the rate of flow can each be varied to cause a partial conversion of the methanol-containing feed. The reactor effluent gas remaining after separation of the formaldehyde can then be recycled into the reactor. It is desirable to add to this gas an amount of pulp mill waste gas to replenish the amount of methanol that has been consumed. In this manner, a continuous circulation can be achieved. If the gas is recirculated in this manner, inert gases and other catalytic reaction products, especially carbon oxides, will concentrate in the recycled gas, and any excessive accumulation of these gases can be prevented by a continuous or discontinuous side-stream removal. It is also desirable to replace the removed exhaust gas with an equal amount of fresh gas.

It The metal oxide of the supported metal oxide catalyst is accommodated in the support primarily as a two-dimensional metal oxide overlayer, with the oxide having a noncrystalline form. Thus, supported metal oxide catalysts useful in the process of this invention generally comprise a metal oxide substrate, such as titania, silica, zirconia, alumina, niobia, ceria, magnesia, lanthanum oxide and tin oxide, whose surface has been modified with a layer of an oxide of a metal or the oxides of a mixture of metals as identified above (e.g., preferably vanadium, and mixtures containing vanadium) in an amount such that the catalyst exhibits properties different from the metal oxide substrate whose surface has not been modified. These catalysts also behave differently from bulk metal oxides of the metal oxide overlayer (e.g., bulk oxides of vanadium, and its mixtures). Consequently, in this embodiment of the invention, the metal oxide loading on the metal oxide support or substrate, e.g., titania, must be sufficient to modify the metal oxide surface, but not enough to result in a catalyst exhibiting properties of the bulk oxides of the metal oxide overlayer, e.g., a bulk oxide of vanadia ($V_2O_5$ or one of its partially reduced forms). Thus, at least a portion of and preferably at least about 25 wt % of the metal oxide coating will be in a noncrystalline form. This will be accomplished if the metal oxide loading on the metal oxide support or substrate broadly ranges between about 0.1 to 35 wt % of the total catalyst weight.

A preferred metal oxide support is titania (titanium dioxide) which can be employed in the anatase or rutile form. For example, at least about 25 wt % (and generally from about 50 to about 100 wt %) of the titanium dioxide ($TiO_2$) can be in the anatase form. As recognized by those skilled in the catalytic art, the titania support material needs to be judiciously evaluated since certain grades may have impurities that interfere with the catalytic activity. Normally, with recognition of the previous caveat, the titanium dioxide may be prepared by any conventional technique. The titanium dioxide used in the catalyst of this invention may be composed of substantially porous particles of a diameter of from about 0.4 to about 0.7 micron and preferably has a specific surface area of at least about 1 $m^2/g$.

The metal oxide supported catalysts of this invention may be prepared by impregnation techniques well-known in the art, such as incipient wetness, grafting, equilibrium adsorption, vapor deposition, thermal spreading, and the like. When using an incipient wetness impregnation technique, an aqueous or nonaqueous solution containing a metal oxide precursor compound is contacted with the metal oxide support or substrate material, such as titania, for a time sufficient to deposit a metal oxide precursor material onto the support such as by selective adsorption or alternatively, excess solvent may be evaporated leaving behind the precursor compound or salt. If an incipient wetness impregnation technique is used to prepare a catalyst of this invention, the metal oxide precursor (such as a salt) solution used may be aqueous or organic, the only requirement being that an adequate amount of a precursor compound for the selected metal oxide be soluble in the solvent used in preparing this solution. Other impregnation techniques, such as vapor deposition and thermal spreading, do not require use of a solvent as does incipient wetness, and may be desirable in some circumstances to avoid the problem of volatile organic carbon (VOC) emissions.

For example, one way to disperse vanadium oxide, tungsten oxide, or a combination of the two oxides onto a titania metal oxide support or substrate is to impregnate titania spheres or powder (spheres or powder are used as representative examples of shapes of titania) with a solution containing a vanadium or a tungsten compound. When impregnating a substrate with both oxides, the tungsten and vanadium are introduced in a stepwise manner, tungsten first, followed by vanadium, with appropriate intermediate drying and calcining steps. Each solution may be an aqueous solution, each may be a solution based on an organic solvent, or one solution may be aqueous and the other organic. Generally, use of an aqueous solution is preferred. Criteria used to choose the vanadium and tungsten compounds include whether the compounds are soluble in the desired solvent and whether the compounds decompose at an acceptable rate at the calcination temperature to give the appropriate metal oxide. Illustrative of suitable compounds of vanadium and tungsten are the halides of vanadium and tungsten, oxyacids, oxyacid salts, and oxysalts of vanadium and tungsten. Specific examples are tungsten dibromide, tungsten pentabromide, tungsten tetrachloride, tungsten dioxydichloride, tungstic acid, ammonium meta-tungstate, vanadium tribromide, vanadium dichloride, vanadium trichloride, vanadium oxychloride, vanadium oxydichloride, vanadic acid, vanadyl sulfate, vanadium alkoxides, vanadium oxalate (which may be formed in situ by reaction of $V_2O_5$ and an aqueous solution of oxalic acid), and ammonium meta-vanadate. Suitable metal oxide precursor compounds for the other metal species suitable for making the supported metal oxide catalysts of this invention are well recognized by those skilled in the catalysis art.

The impregnation of the metal oxide support or substrate, e.g., titania support spheres or powdered, with the metal oxide precursor compound solution may be carried out, as noted above, in ways well known in the art using either wet or dry impregnation techniques. One convenient method is to place the metal oxide support or substrate, e.g., titania particles, into a rotary evaporator which is equipped with a steam jacket. An impregnating solution of a precursor compound which contains an amount of the desired metal to be included in the finished catalyst (as the metal) is added to the support particles and the mixture is cold rolled (no steam) for a time from about 10 to 60 minutes sufficient to impregnate the support with the precursor compound solution. Next, steam is introduced and the solvent is evaporated from the impregnated solution. This usually takes from about 1 to about 4 hours. The impregnated support will normally be dried at temperatures ranging from about 50°–300° C. to remove excess solvent.

Water-soluble precursor compounds are generally preferred for industrial applications because of the environmental concern about VOC emissions. Nonetheless, when using an organic solvent, initial heating may be done in a nitrogen atmosphere to remove any flammable solvent. Finally, the support particles are removed from the rotary evaporator and calcined in a suitable oxidizing atmosphere such as air, oxygen, etc. at a temperature of about 150° to 800° C., and more usually from 400°–600° C., preferably for about 1 to about 3 hours, sufficient to decompose the precursor compound to the corresponding metal oxide. In other cases, as recognized by those skilled in the art, calcining conditions need to be adjusted to avoid undesirably reducing the catalyst surface area or transforming the oxide supports via solid state reactions.

Because some precursor compounds are air/moisture sensitive, they are prepared under a nitrogen atmosphere, as is recognized by those skilled in this art. The time required to calcine the composite will, of course, depend on the temperature and, in general, may broadly range from about 0.5–16 hours, though calcination times of less than 7 hours may often be suitable. Calcination at 450° C. for about 2 hours has proven to be suitable for 1% vanadia on titania catalyst. The precise time and temperature for calcination depends on the particular metal oxide overlayer and should be selected to avoid adversely affecting the metal oxide support, e.g., in the case of a titania metal oxide support, to avoid substantial crystal phase transformation of the anatase into another crystalline form, such as rutile and decreasing the surface area of the titania.

Reducing atmospheres may also be used to decompose the transition metal oxide precursors, but the resulting composite will then require subsequent calcination to convert the reduced metal component to the oxide form. If the support is to be provided with an overlayer of a combination of metal oxides, e.g., if an overlayer containing both vanadium and tungsten oxide is desired, then the metal oxide precursor compounds may be impregnated on the metal oxide support simultaneously, but preferably are impregnated sequentially as previously noted.

The metal oxide supported catalysts of this invention will generally have surface metal oxide loadings of from about 0.1 to 35 wt. % metal oxide based on the total active catalyst composition, preferably from about 1 to 20 wt. %, more usually from about 1–15 wt. %, and most preferably 1–10 wt. % based on the total active catalyst composition.

While titania, silica, zirconia, alumina, niobia, ceria, magnesia, lanthanum oxide and tin oxide are conveniently referred to as supports or substrates in the description of the preferred embodiment of the present invention, based to a large degree on the way the catalyst is prepared, it should be noted that they provide important roles as active catalytic components in the supported metal oxide catalyst. Combination supports may also be advantageous. For example, substrates constituting a mixture of titania and zirconia or titania and silica can be used.

Further details on the preparation and structure of such metal oxide supported catalysts useful in the practice of the present invention can be found in Jehng et al., *Applied Catalysis A*, 83, (1992) 179–200; Kim and Wachs, *Journal of Catalysis*, 142, 166–171; Jehng and Wachs, *Catalysis Today*, 16, (1993) 417–426; Kim and Wachs, *Journal of Catalysis*, 141, (1993) 419–429; Deo et al., *Applied Catalysis A*, 91, (1992) 27–42; Deo and Wachs, *Journal of Catalysis*, 146, (1994) 323–334; Deo and Wachs, *Journal of Catalysis*, 146, (1994) 335–345; Jehng et al., *J. Chem. Soc. Faraday Trans.*, 91(5), (1995) 953–961; Kim et al., *Journal of Catalysis*, 146, (1994) 268–277; Banares et al., *Journal of Catalysis*, 150, (1994) 407–420 and Jehng and Wachs, *Catalyst Letters*, 13, (1992) 9–20, the disclosures of which are incorporated herein by reference.

Preferred supported metal oxide catalysts are those which are known to be suitable for converting methanol to formaldehyde. Particularly preferred are supported metal oxide catalysts comprising a vanadia overlayer on a titania support.

It often is desired that the metal oxide, such as titania, silica, zirconia, alumina niobia, magnesia, ceria, lanthanum oxide, tin oxide, and their mixtures, used as a catalyst support component in accordance with the present invention have a surface area in the range of about 10 to about 150 $m^2/g$ and higher. These materials may be used in any configuration, shape or size which exposes their surface and any metal oxide layer dispersed thereon to the gaseous stream passed in contact therewith. For example, these oxide supports, such as titania can conveniently be employed in a particulate form or deposited (before or after impregnation with the metal oxide overlayer) on a monolithic carrier or onto ceramic rings or pellets. As particles, the support, such as titania, can be formed in the shape of pills, pellets, granules, rings, spheres and the like. Use of free particulates might be desirable when large catalyst volumes are needed or if the catalyst bed is operated in a fluidized state. A monolithic form or deposition of the active catalyst on an inert ceramic support might be preferred in applications where catalyst movement is to be avoided because of concerns about catalyst attrition and dusting, and a possible increase in pressure drop across a particulate bed. In a preferred approach, a metal oxide supported catalyst, such as a vanadia on titania catalyst, may be deposited on a ceramic or refractory inorganic carrier such as silicon carbide, silicon nitride, carborundum, steatite, alumina and the like, provided in the shape of rings or pellets. Typically, the active catalyst will be applied to the inert ceramic support in an amount to provide 1 to 20% by weight, and preferably 5 to 15%, of the supported catalyst.

Within the broad practice of the invention, the catalytic reactor can be supplied with a single catalyst composition or combinations of multiple metal oxide supported catalysts can be used.

EXAMPLES

To facilitate a more complete understanding of the invention, a number of Examples are provided below. The scope of the invention, however, is not limited to specific embodiments disclosed in these Examples, which are for purposes of illustration only.

Catalyst Preparation and Characterization

Supported metal oxide catalysts were prepared as follows:

Preparation Example 1: Vanadia on Titania

A vanadia (~1.15% by weight) on titania metal oxide supported catalyst was prepared in accordance with the following procedure. The vanadia-titania catalyst was prepared by using $TiO_2$ (Degussa P25) as the support. The $TiO_2$ support (~10% rutile and ~90% anatase) possessed a surface area of ~55 $m^2/g$. It was calcined in air at 500° C. and cooled to room temperature before impregnation with the vanadium oxide precursor. The vanadium oxide overlayers on the $TiO_2$ support were prepared from vanadium triisopropoxide oxide (Alfa, 95–98% purity) by the incipient wetness impregnation method. The preparation was performed under a nitrogen environment and in nonaqueous solutions, since the alkoxide precursor is air and moisture sensitive. Solutions of known amounts of vanadium triisopropoxide oxide and propanol-2, corresponding to the incipient wetness impregnation volume and the final amount of vanadium required, were prepared in a glove box filled with nitrogen. The solutions of the vanadium precursor and propanol-2 were then thoroughly mixed with the titania support and dried at room temperature in the glove box for 24 hr. The impregnated samples were heated to 300° C. in flowing nitrogen and the final calcination was performed in $O_2$ (Linde, 99.9% pure) at 500° C. for 15 hours. The catalyst was then pelletized, crushed and sieved to obtain catalyst particles sizes between 100 to 200 $\mu$m.

Using substantially the same procedure as above (except that the final calcination was carried out at 450° C. for 2 hours), catalysts containing about 3% by weight and 5% by weight vanadia on titania were also produced.

Preparation Example 1A: Vanadia on Titania

Another vanadia on titania metal oxide supported catalyst was prepared using the general procedure of Preparation Example 1 except that the final calcination was conducted at 450° C. for 2 hours.

Prepartion Example 2: Molybdenum Oxide on Titania

An aqueous solution of ammonium heptamolybdate $(NH_4)_6Mo_7O_{24}\cdot 4H_2O$ (Alfa) was deposited onto $TiO_2$ (Degussa P25) as the support (~10% rutile and ~90% anatase) by the incipient wetness technique. As in Example 1, the support was calcined in air at 500° C. and cooled to room temperature before impregnation with the molybdenum oxide precursor. The support possessed a surface area of ~55 $m^2/g$. After impregnation, the wet samples were dried at room temperature for 16 hours, further dried at 110–120° C. for 16 hours, and calcined at 450° C. for 12 hours. The catalyst was then pelletized, crushed and sieved to obtain catalyst particles sizes between 100 to 200 $\mu$m.

Preparation Example 3: Chromia on Titania

An aqueous solution of chromium nitrate $(Cr(NO_3)_3 \cdot 9H_2O)$ (Allied Chemical Co.) was deposited onto $TiO_2$ (Degussa P25) as the support using the incipient wetness technique. As in the previous Examples, the $TiO_2$ support (~10% rutile and ~90% anatase) was calcined in air at 500° C. and cooled to room temperature before impregnation with the chromium precursor. The support possessed a surface area of ~55 m$^2$/g. After impregnation, the wet samples were dried at room temperature for 16 hours, further dried at 110–120° C. for 16 hours and calcined at 450° C. for 13 hours. The catalyst was then pelletized, crushed and sieved to obtain catalyst particles sizes between 100 to 200 μm.

Preparation Example 4: Rhenium Oxide on Titania

An aqueous solution of perrhenic acid (HReO$_4$) (Aldrich) was deposited onto TiO$_2$ (Degussa P25) as the support using the incipient wetness technique. As before, the TiO$_2$ support (~10% rutile and ~90% anatase) was calcined in air at 500° C. and cooled to room temperature before impregnation with the rhenium oxide precursor. The support possessed a surface area of ~55m$^2$/g. After impregnation, the wet samples were dried at room temperature for 16 hours, further dried at 110–120° C. for 16 hours and calcined at 450° C. for 13 hours. The catalyst was then pelletized, crushed and sieved to obtain catalyst particles sizes between 100 to 200 μm.

Preparation Example 5: Vanadia on Zirconia

A vanadium oxide overlayer was deposited onto a zirconium oxide (ZrO$_2$) support (Degussa) having a surface area ~39 m$^2$g$^{-1}$ using an organic solution of vanadium triisopropoxide oxide (Alfa, 95–98% purity). In particular, the vanadium overlayer was prepared by the incipient wetness impregnation method using a solution of vanadium triisopropoxide oxide and propanol-2 in a glove box filled with nitrogen. The solutions of the vanadium precursor and propanol-2 were thoroughly mixed with the zirconia support and dried at room temperature for 16 hours, further dried at 110–120° C. for 16 hours and calcined at 450° C. for 16 hours. The catalyst was then pelletized, crushed and sieved to obtain catalyst particles sizes between 100 to 200 μm.

Preparation Example 6: Vanadia on Niobia

A vanadium oxide overlayer was deposited on a niobia (Nb$_2$O$_5$) support (55 m$^2$g$^{-1}$) using vanadium triisopropoxide oxide (Alfa, 95–98% purity) and the incipient wetness technique. The niobia support was prepared by calcining niobic acid (Niobia Products Co.) at 500° C. for two hours. A solution of vanadium triisopropoxide oxide and propanol-2 was thoroughly mixed with the niobia support in a glove box filled with nitrogen, dried at room temperature for 16 hours, further dried at 110–120° C. for 16 hours and calcined at 450° C. for 16 hours. The catalyst was then pelletized, crushed and sieved to obtain catalyst particles sizes between 100 to 200 μm.

Preparation Example 7: Vanadia on Alumina

A vanadium oxide overlayer was deposited on an alumina (Al$_2$O$_3$) support (Harshaw, 180 m$^2$g$^{-1}$) using an organic solution of vanadium triisopropoxide oxide (Alfa, 95–98% purity) and the incipient wetness impregnation. A solution of the vanadium precursor and propanol-2 was thoroughly mixed with the alumina support, in a glove box filled with nitrogen, dried at room temperature for 16 hours, further dried at 110–120° C. for 16 hours and calcined at 500° C. for 16 hours. The catalyst was then pelletized, crushed and sieved to obtain catalyst particles sizes between 100 to 200 μm.

Preparation Example 8: Vanadia on Silica

A vanadium oxide overlayer was deposited on an silica (SiO$_2$) support (Cab-O-Sil, 300 m$^2$g$^{-1}$) using an organic solution of vanadium triisopropoxide oxide (Alfa, 95–98% purity) and the incipient wetness impregnation. A solution of the vanadium precursor and propanol-2 was thoroughly mixed in a glove box filled with nitrogen with the SiO$_2$ support, the wet silica was dried at room temperature for 16 hours, further dried at 110–120° C. for 16 hours and calcined at 500° C. for 16 hours. The catalyst was then pelletized, crushed and sieved to obtain catalyst particles sizes between 100 to 200 μm.

Preparation Example 9: Titania Oxide on Silica

An aqueous solution of ammonium metatungstate ((NH$_4$)$_6$ H$_2$W$_{12}$O$_{40}$.xH$_2$O) (Pfaltz & Bauer, 99.9% purity) was deposited as an oxide overlayer onto a silica (SiO$_2$) support (Cab-O-Sil, 300 m$^2$g$^{-1}$) using the incipient wetness technique. After impregnation, the silica support was dried at room temperature for 16 hours, further dried at 110–120° C. for 16 hours and calcined at 500° C. for 16 hours. The catalyst was then pelletized, crushed and sieved to obtain catalyst particles sizes between 100 to 200 μm.

Preparation Example 10: Niobia on Silica

An aqueous solution of niobium oxalate (Niobium Products Co.) was deposited onto a silica (SiO$_2$) support (Cab-O-Sil, 300 m$^2$g$_{-1}$) using the incipient wetness technique. After impregnation, the silica support was dried at room temperature for 16 hours, further dried at 110–120° C. for 16 hours and calcined at 500° C. for 16 hours. The catalyst was then pelletized, crushed and sieved to obtain catalyst particles sizes between 100 to 200 μm.

Preparation Example 11: Titania on Silica

Titanium isopropoxide (Aldrich) in a toluene solution was impregnated onto a silica (SiO$_2$) support (Cab-O-Sil, 300 m$^2$g$^{-1}$) under a nitrogen blanket to form a titania overlayer using the incipient wetness technique. After impregnation, the wet silica was dried at room temperature for 16 hours, further dried at 110–120° C. for 16 hours and calcined at 500° C. for 16 hours. The catalyst was then pelletized, crushed and sieved to obtain catalyst particles sizes between 100 to 200 μm.

Preparation Example 12: Vanadia and Tungsten Oxide on Titania

A vanadia and tungsten oxide on titania catalyst was prepared by a two step incipient wetness impregnation method. A vanadium oxide overlayer was deposited first on the TiO$_2$ support using a solution of vanadium triisopropoxide oxide (Alfa, 95–98% purity) and propanol-2 by the incipient wetness impregnation method in a glove box filled with nitrogen. The solution of the vanadium precursor and propanol-2 were thoroughly mixed with the TiO$_2$ (Degussa P25) as the support. The TiO$_2$ support (~10% rutile and ~90% anatase) was prepared by previous calcination in air at 500° C. and cooled to room temperature before impregnation with the vanadium oxide precursor. The support possessed a surface area of ~55 m$^2$/g. After impregnation, the wet TiO$_2$ was dried at room temperature for 16 hours, further dried at 110–120° C. for 16 hours and calcined at 450° C. for 12 hours. Subsequently, an aqueous solution of ammonium metatungstate (NH$_4$)$_6$H$_2$W$_{12}$O$_{40}$.xH$_2$O) was deposited as an oxide overlayer onto the TiO$_2$ support, again using the incipient wetness technique. After impregnation, the wet samples were dried at room temperature for 16 hours, further dried at 110–120° C. for 16 hours and calcined at 500° C. for 16 hours. The catalyst was then pelletized, crushed and sieved to obtain catalyst particles sizes between 100 to 200 μm.

Preparation Example 13: Vanadia and Titania on Silaca

A vanadia and titania on silica catalyst was prepared by a two step incipient wetness impregnation method. The silica support used for this study was Cabosil EH-5 (380 m$^2$/g). This fluffy material was treated with water in order to condense its volume for easier handling. Then the wet $SiO_2$ was dried at 120° C. and subsequently calcined at 500° C. overnight. The resulting surface area was 332 m$^2$/g. This water pretreatment did not change the dispersion ability of the silica, since an isopropanol pretreated silica also resulted in the same surface area and the same dispersion capacity. A titanium oxide overlayer was deposited first on the silica ($SiO_2$) support under a nitrogen blanket using titanium isopropoxide (Aldrich) in a toluene solution by the incipient wetness impregnation method in a glove box filled with nitrogen. After impregnation, the loaded sample was dried at room temperature for 16 hours, further dried at 110–120° C. for 16 hours and calcined at 500° C. for 4 hours. Subsequently, a solution of vanadium triisopropoxide oxide (Alfa, 95–98% purity) and propanol-2 was impregnated onto the silica ($SiO_2$) support containing titania again using the incipient wetness technique. The solution of the vanadium precursor and propanol-2 was thoroughly mixed with the $SiO_2$ support containing titania. After impregnation, the wet $SiO_2$ was dried at room temperature for 16 hours, further dried at 110–120° C. for 16 hours and calcined at 450° C. for 2 hours. The catalyst was then pelletized, crushed and sieved to obtain catalyst particles sizes between 100 to 200 μm.

Certain of the above-synthesized catalysts were examined for their ability to oxidize methanol selectively to formaldehyde generally using the following equipment and methods. The performance of the catalyst in the presence of other likely constituents of pulp mill waste streams were also examined.

Catalytic Reactor

The oxidation reactions were carried out in an isothermal fixed-bed integral mode reactor operating at atmospheric pressure. The reactant gases were supplied in admixture with helium and were further diluted in helium and air (Blue Valley Welding Supply, total hydrocarbons concentration <1 ppm, $H_2O$ concentration <3 ppm) and sent to the catalytic reactor through glass tubing connected with Teflon fittings. Flow rates and concentrations were controlled by two mass flow controllers (Brooks 5850 D, 1–100 sccm for helium and Omega FMA-767-V, 0–1 slpm for the other gas feed streams). The lines were heated to 70° C.–110° C. to prevent condensation. The total gas flow was maintained between 150 and 200 ml/min. The reactor was kept in a vertical position and made of 6-mm O.D. Pyrex glass. Heating tape was used in conjunction with a feedback temperature controller (Omega CN 9000) to obtain the desired reactor temperature. The catalysts were held at the middle of the reactor tube between a porous glass fiit, pore size of 40 to 60 μm, and a glass wool plug. Each catalyst sample was always pretreated by heating at 500° C. for 2 to 3 hours in flowing air, to remove adsorbed water on the catalyst surface prior to initiation of an experiment. The outlet of the reactor was connected to an FTIR cell (Infrared Analysis, Inc; Model #G-4-Tin-Ta-Ba-Ag), which was used to analyze the reaction products. The lines between the outlet and the cell were heated to avoid condensation of the products. The flow of reaction products sent to the FTIR cell was controlled by a needle valve (Nupro Company, SS-4BRG).

Composition Analysis by FTIR

Analysis of the reaction products was accomplished using a Midac Inc. FTIR, (model #101250, series 2–4). Samples were analyzed in a path gas cell (Infrared Analysis, Inc; Model # G-4-Tin-Ta-Ba-Ag), which has an effective length of 10 m and a volume of 3.1 L. The spectrometer was controlled by a microcomputer (Sprouse Scientific, model TECH- 1000 A) to provide acquisition and manipulation of the spectra: display, subtraction, zoom, etc. The spectra were obtained using 16 scans at a resolution of 0.5 cm$^{-1}$. The FTIR analysis required about 10 minutes.

Example 1

Figure 2:
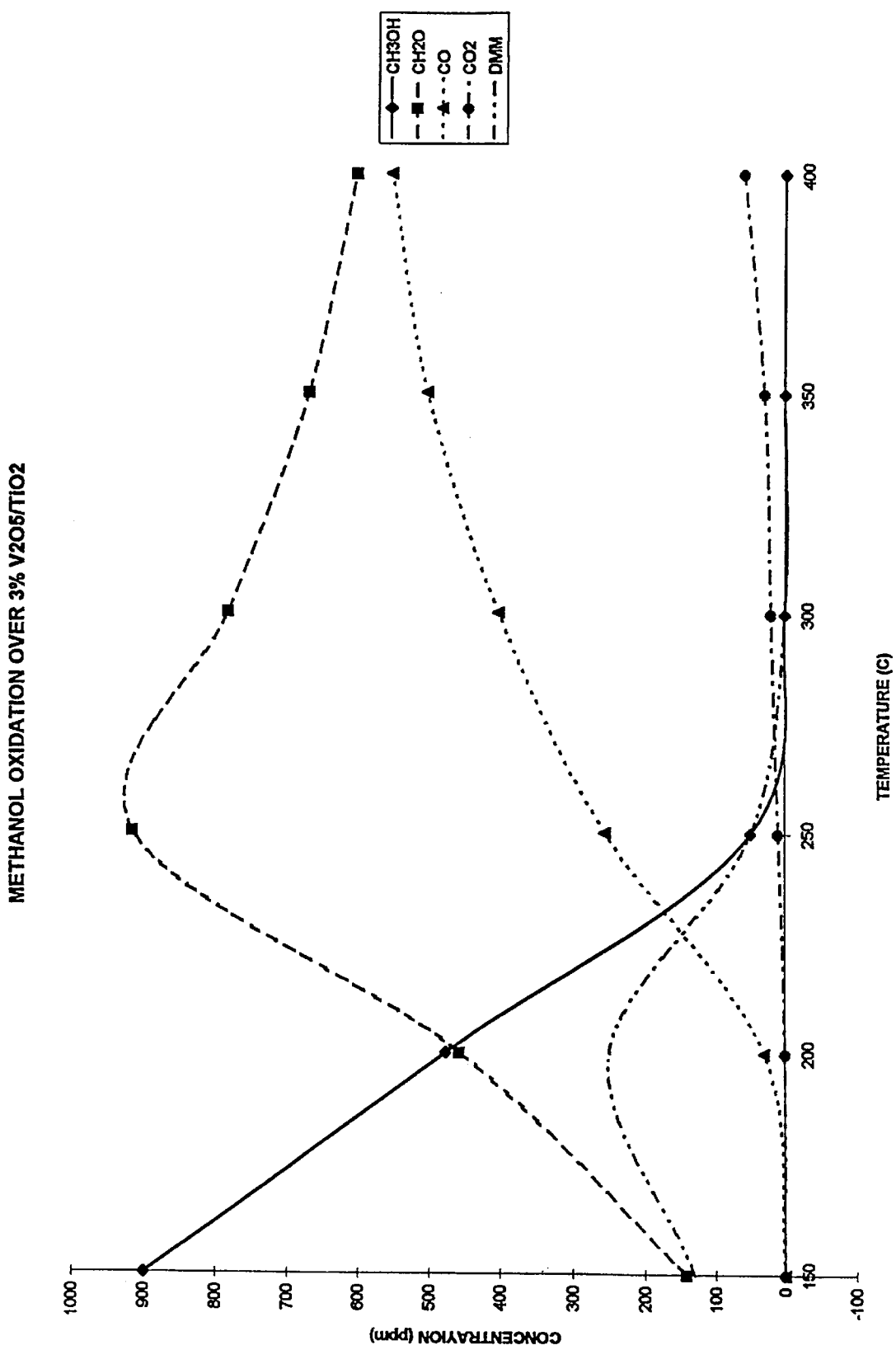
FIG. 2 illustrates the distribution of products produced by oxidizing methanol over a vanadia on titania catalyst containing about 3% by weight vanadia over the temperature range of 150° to 400° C.
Figure 3:
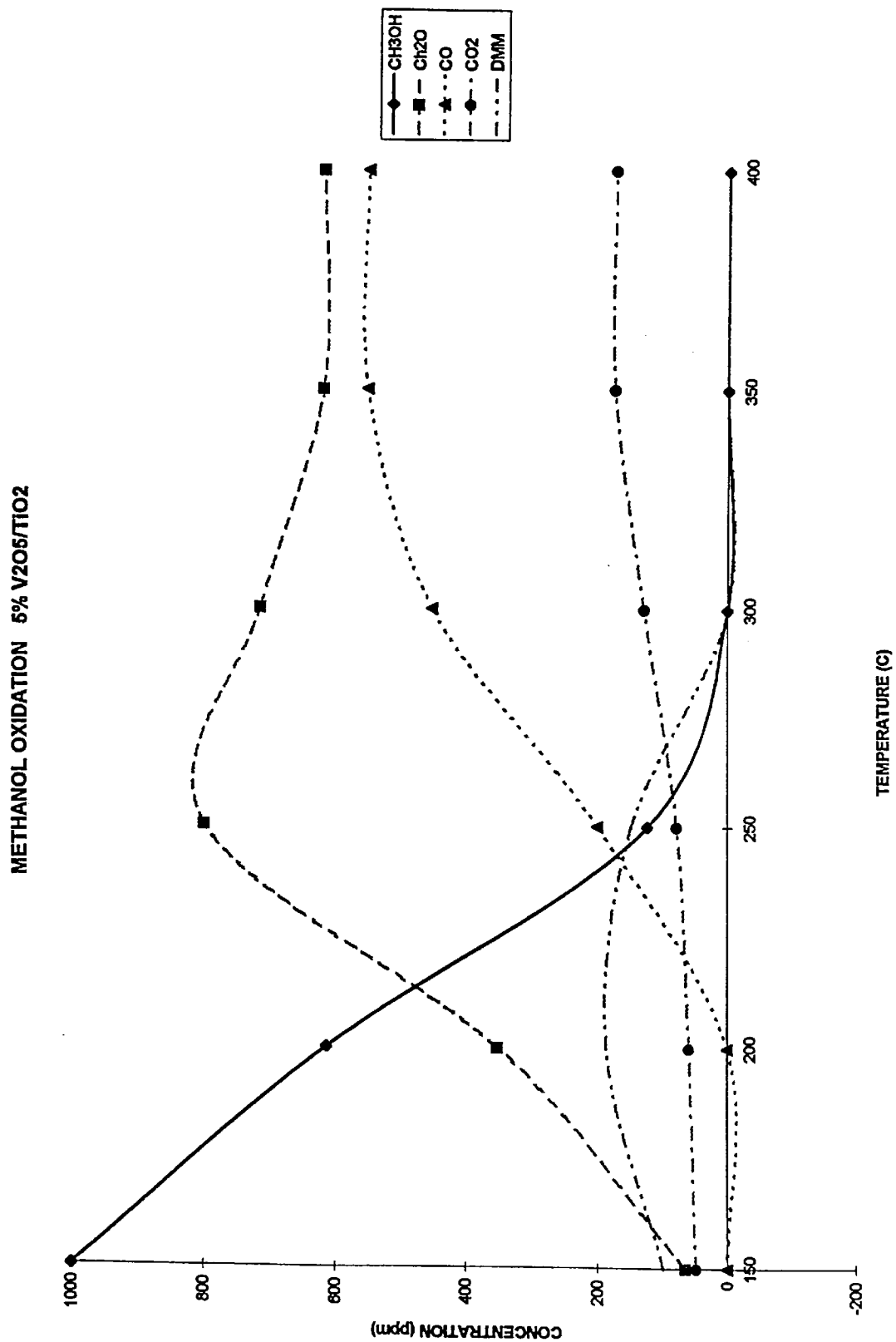
FIG. 3 illustrates the distribution of products produced by oxidizing methanol over a vanadia on titania catalyst containing about 5% by weight vanadia over the temperature range of 150° to 400° C.

In a series of experiments, 10 mg of supported metal oxide catalysts prepared in accordance with Preparation Example 1, comprising about 1%, 3% and 5% vanadia ($V_2O_5$) on titania ($TiO_2$) catalysts, were contacted with a gas containing 1200 ppm methanol (Scott Specialty Gases) and oxygen, over a wide temperature range, in order to optimize the formation of formaldehyde. The gas stream was passed in contact with the catalyst at a flow rate of 150 ml/min. Methanol conversion was measured by both increasing and decreasing the temperature between 150 and 450° C., and no temperature hysteresis was observed. The reaction products of this methanol oxidation over the 1%, 3% and 5% $V_2O_5$/$TiO_2$ catalysts, as a function of temperature, are graphically presented in FIGS. 1, 2 and 3, respectively. As illustrated, formaldehyde was found to be the predominant product, while at higher temperatures an increasing amount decomposed to carbon monoxide which further oxidized to carbon dioxide. In these tests, dimethoxymethane ($H_2C(OCH_3)_2$) was observed as an intermediate between 250 to about 300° C. The 3% and 5% catalyst loadings were less selective for formaldehyde than the 1% vanadia overlayer catalyst due to greater decomposition of formaldehyde to carbon oxides.

Example 2

Figure 4:
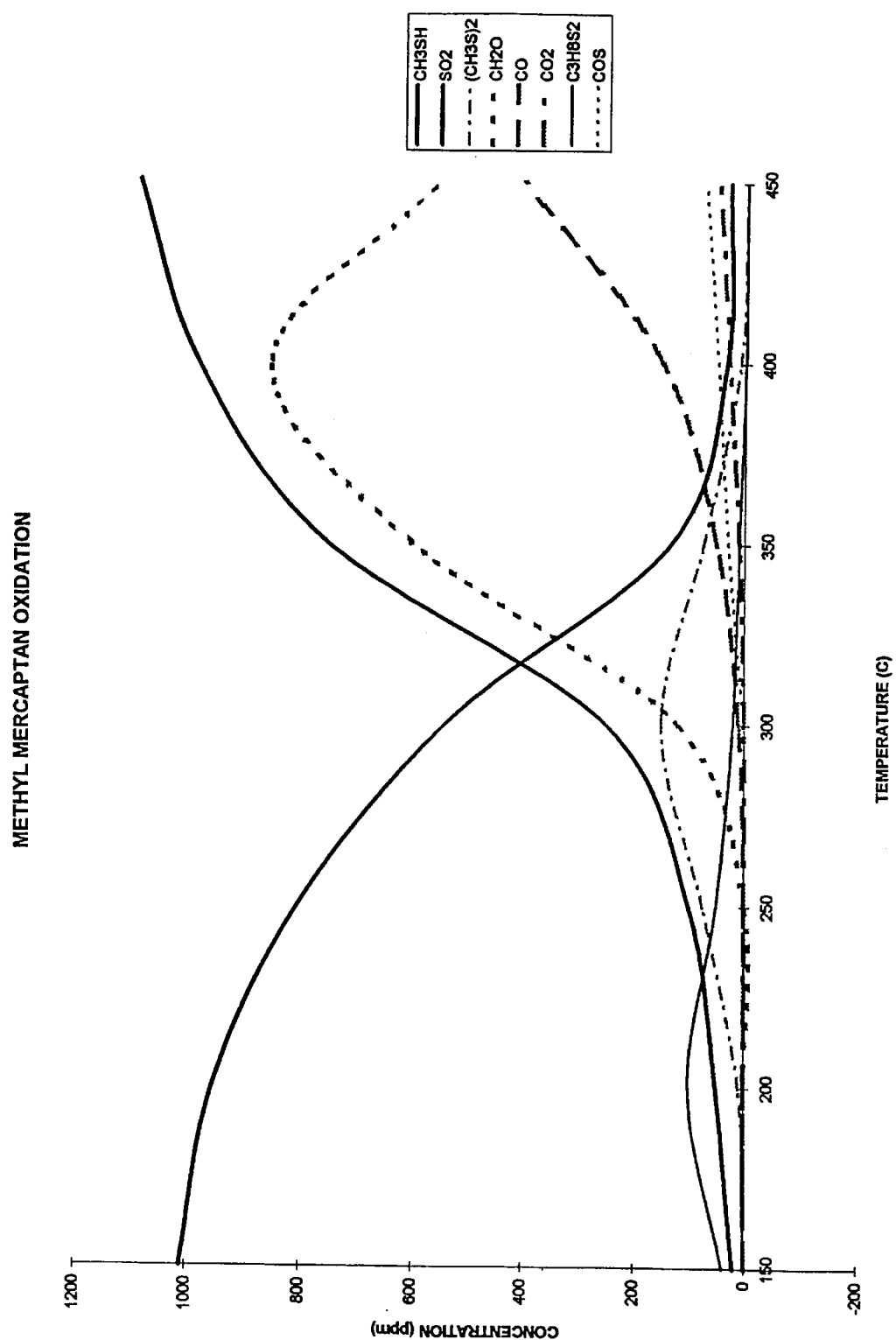
FIG. 4 illustrates the distribution of products produced by oxidizing methanethiol over a vanadia on titania catalyst containing about 1% by weight vanadia over the temperature range of 150° to 450° C. Maximum selectivity for the conversion of methanethiol to formaldehyde was observed at a temperature of about 400° C. Starting at about 300° C., there was a significant conversion of methanethiol to formaldehyde.

In a series of experiments, 10 mg of a supported oxide catalyst prepared in accordance with Preparation Example 1, comprising about 1% vanadia ($V_2O_5$) on titania ($TiO_2$) catalyst, was contacted with a gas stream containing 1150 ppm methanethiol, in the presence of oxygen, over a wide temperature. The gas stream was passed in contact with the catalyst at a flow rate of 150 ml/min. Conversion of the mercaptan to formaldehyde was observed. Mercaptan conversions were measured by both increasing and decreasing the temperature between 200 and 450° C., and no temperature hysteresis was observed. The reaction products of this methanethiol oxidation over the 1% $V_2O_5$/$TiO_2$ catalyst as a function of temperature is graphically presented in FIG. 4. As illustrated, formaldehyde was found to be the predominant product. In these tests, dimethylthiomethane ($H_2C(SCH_3)_2$) was observed as an intermediate between 200 to 300° C., and dimethyl disulfide ($CH_3S)_2$ was found as an intermediate between 300 to 400° K. Carbon monoxide, carbon dioxide and COS appeared in small amounts as reaction products; but the formation of CO increased at elevated temperatures. Sulfur dioxide production tracked the formation of formaldehyde.

Figure 5:
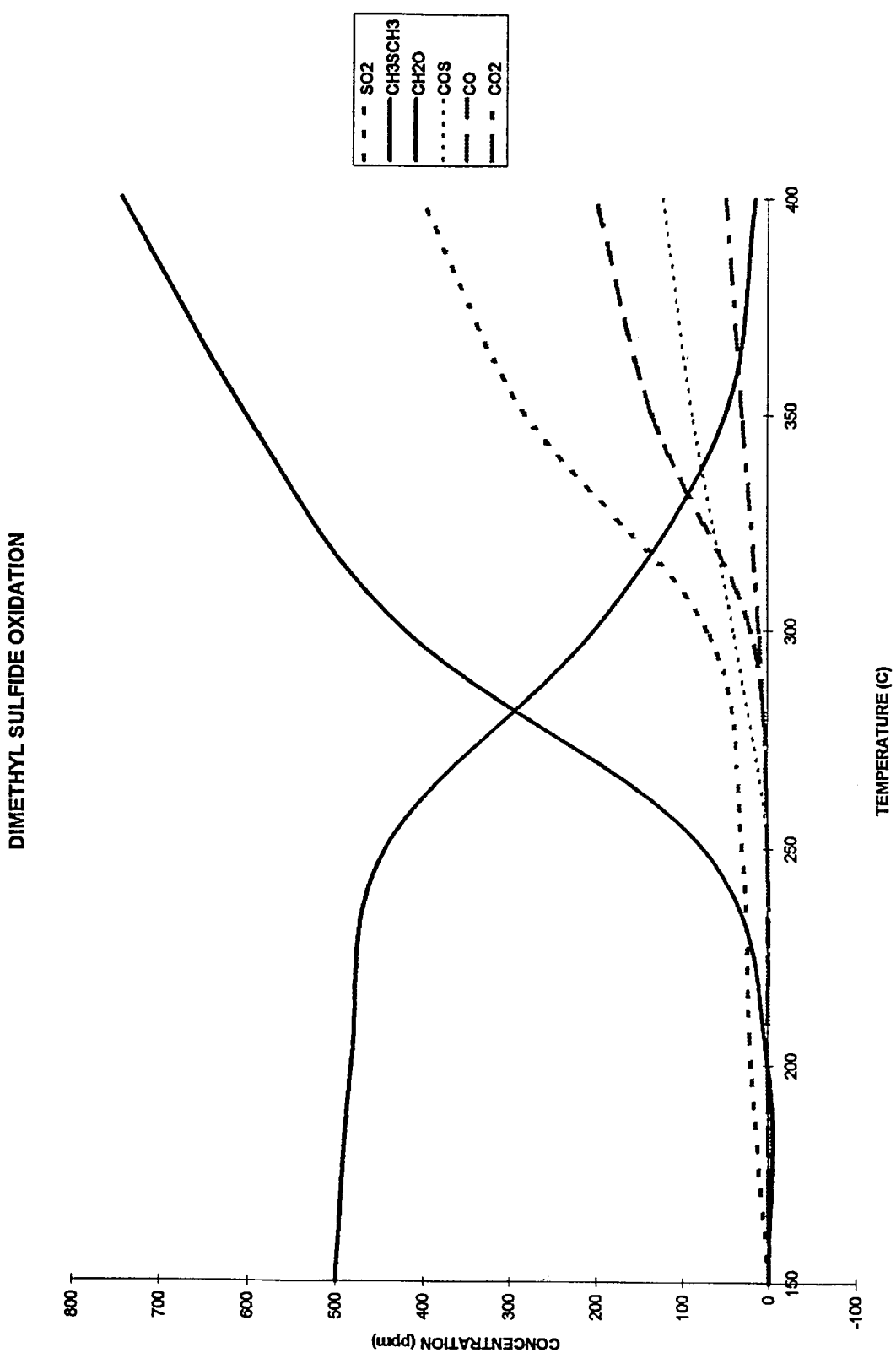
FIG. 5 illustrates the distribution of products produced by oxidizing dimethyl sulfide over a vanadia on titania catalyst containing about 1% by weight vanadia over the temperature range of 150° to 400° C.
Figure 6:
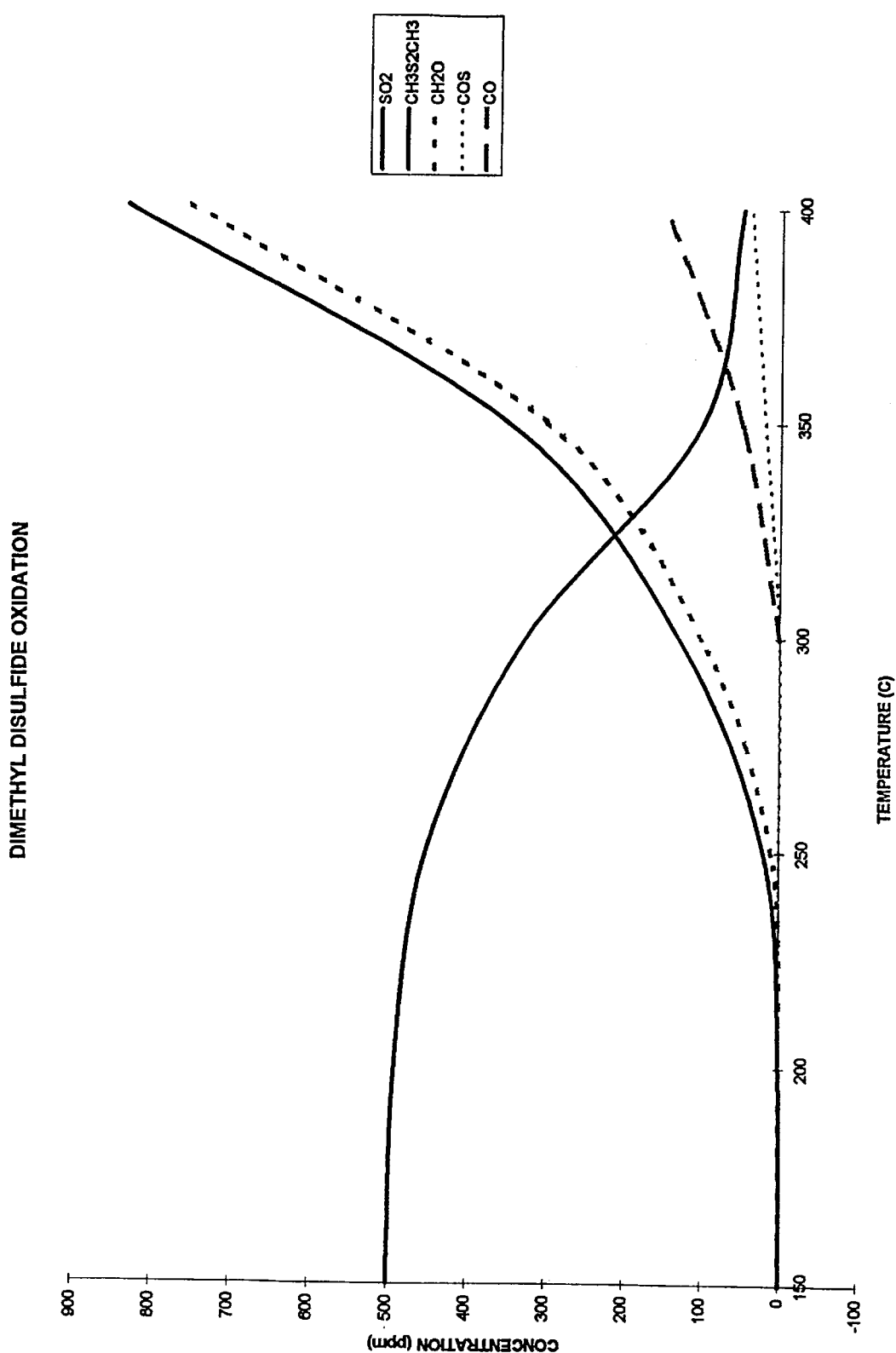
FIG. 6 illustrates the distribution of products produced by oxidizing dimethyl disulfide over a vanadia on titania catalyst containing about 1% by weight vanadia over the temperature range of 150° to 400° C.

The same equipment and procedures (e.g. flow rate) were used to examine the behavior of dimethyl sulfide (513 ppm) and dimethyl disulfide (490 ppm) over the same catalyst and a similar temperature range. The results are shown, respectively, in FIGS. 5 and 6.

Example 3

Figure 7:
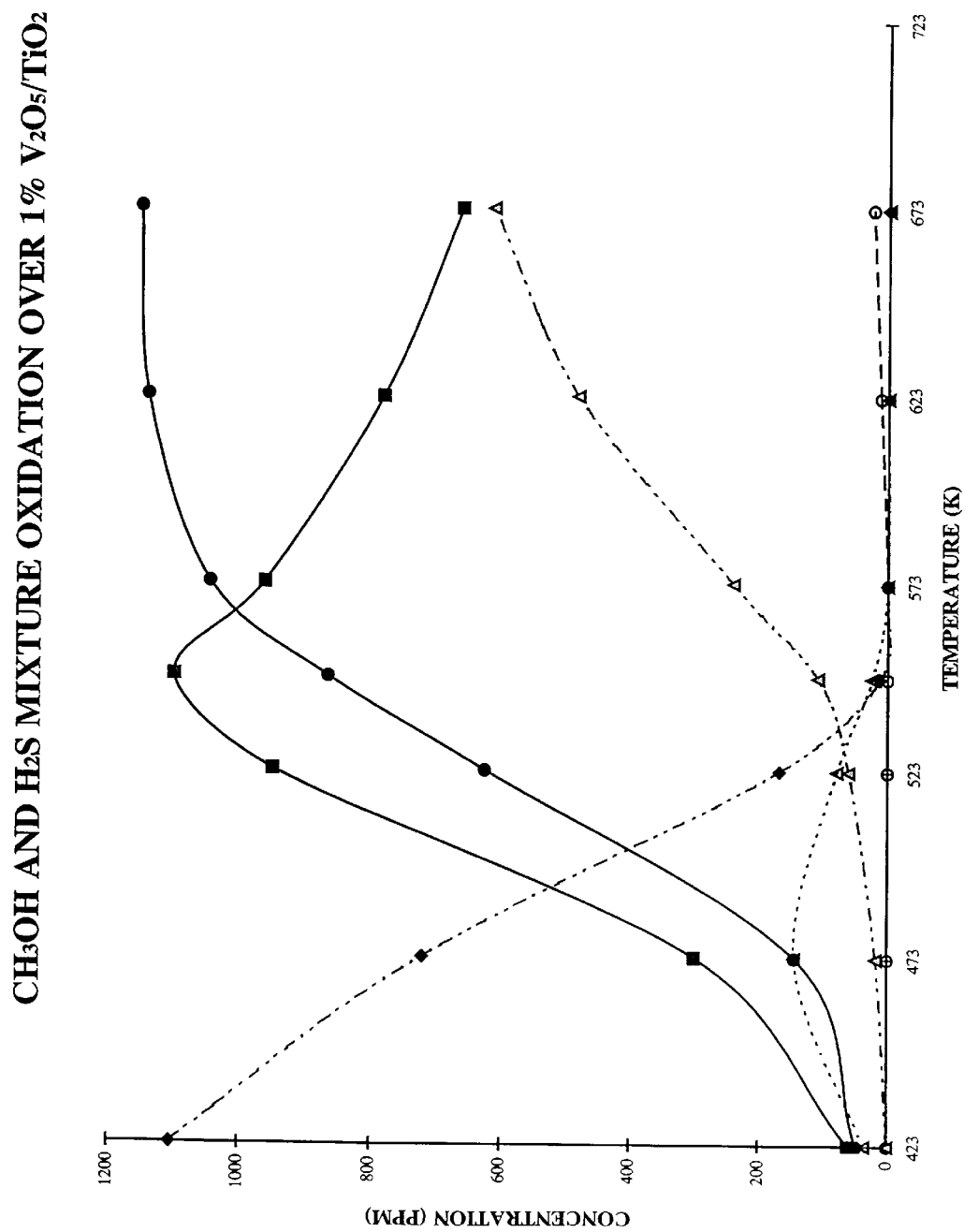
FIG. 7 illustrates the distribution of products produced by oxidizing a mixture of methanol and hydrogen sulfide over a vanadia on titania catalyst containing about 1% by weight vanadia over the temperature range of 150° to 400° C.
Figure 8:
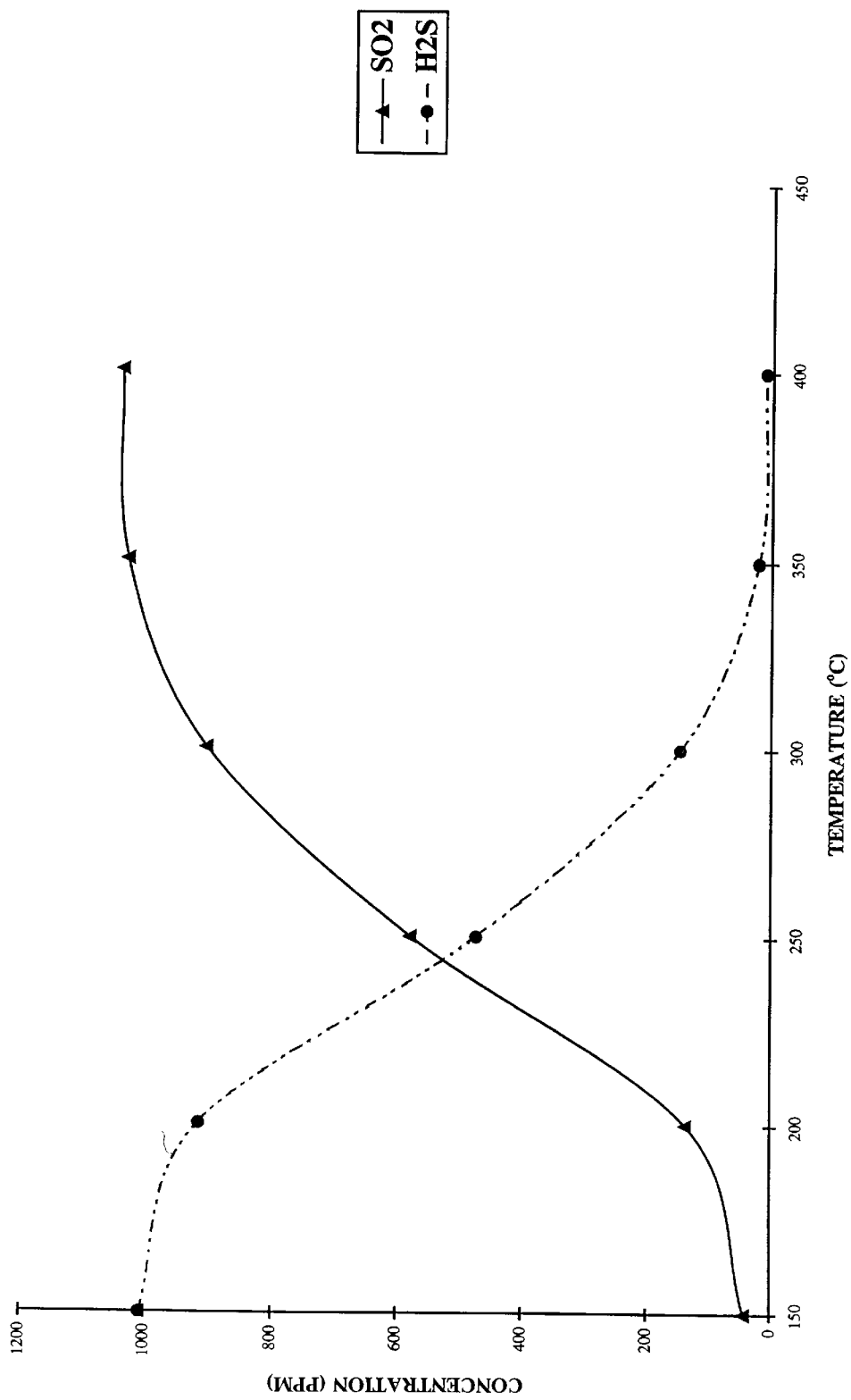
FIG. 8 illustrates the distribution of products produced by oxidizing hydrogen sulfide over a vanadia on titania catalyst containing about 1% by weight vanadia over the temperature range of 150° to 400° C.
Figure 9:
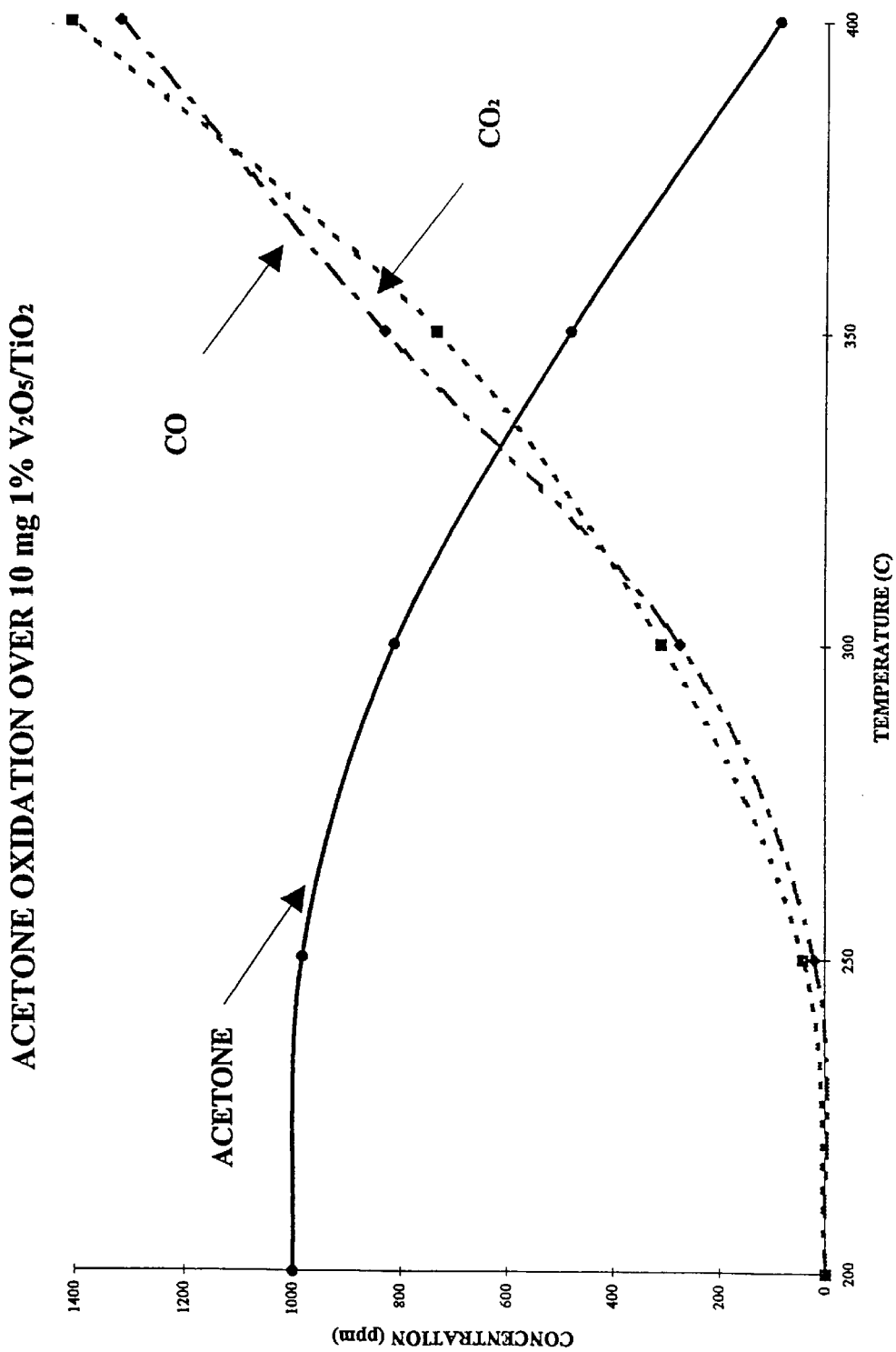
FIG. 9 illustrates the distribution of products produced by oxidizing acetone over a vanadia on titania catalyst containing about 1% by weight vanadia over the temperature range of 200° to 400° C.
Figure 10:
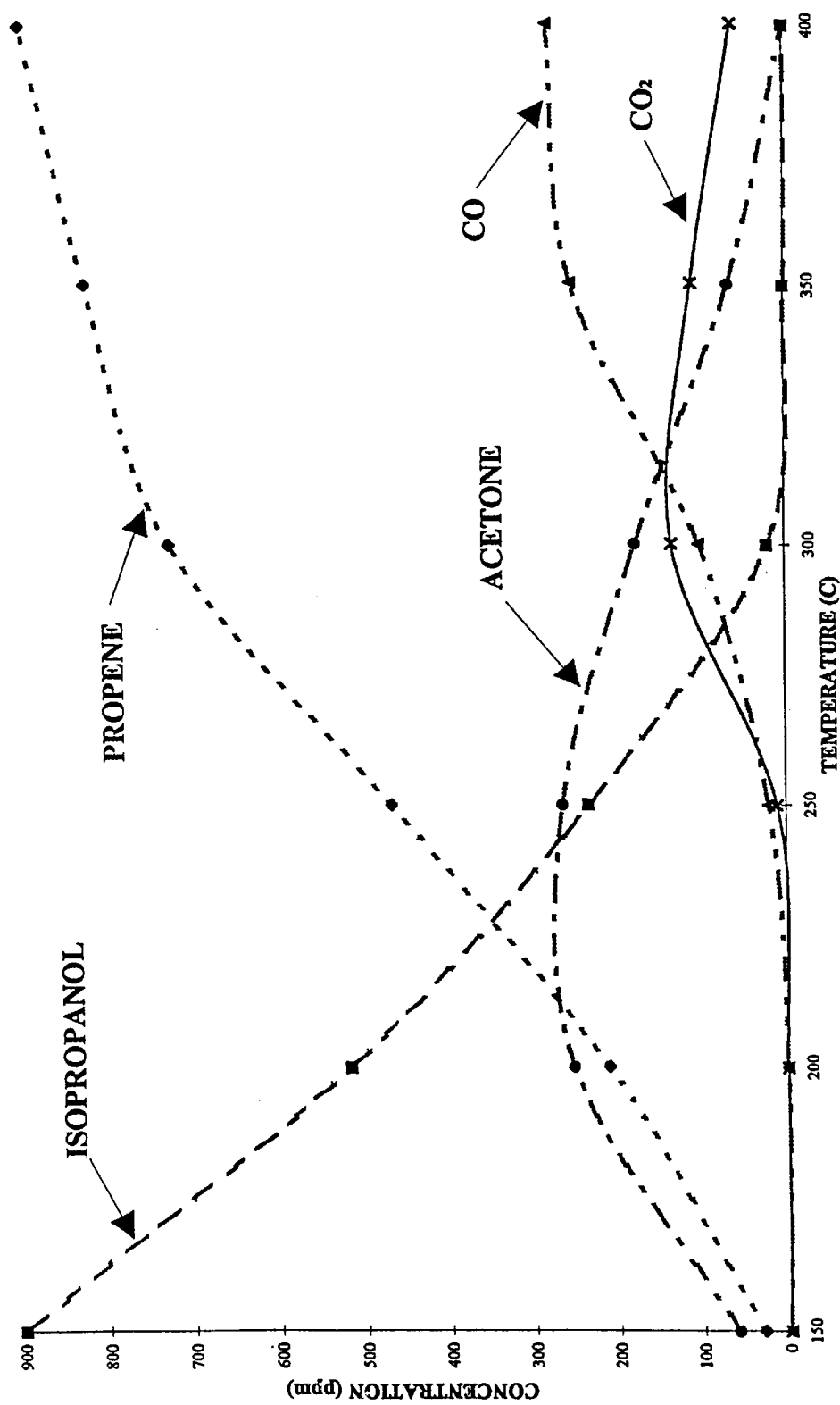
FIG. 10 illustrates the distribution of products produced by oxidizing isopropanol over a vanadia on titania catalyst containing about 1% by weight vanadia over the temperature range of 150° to 400° C.
Figure 11:
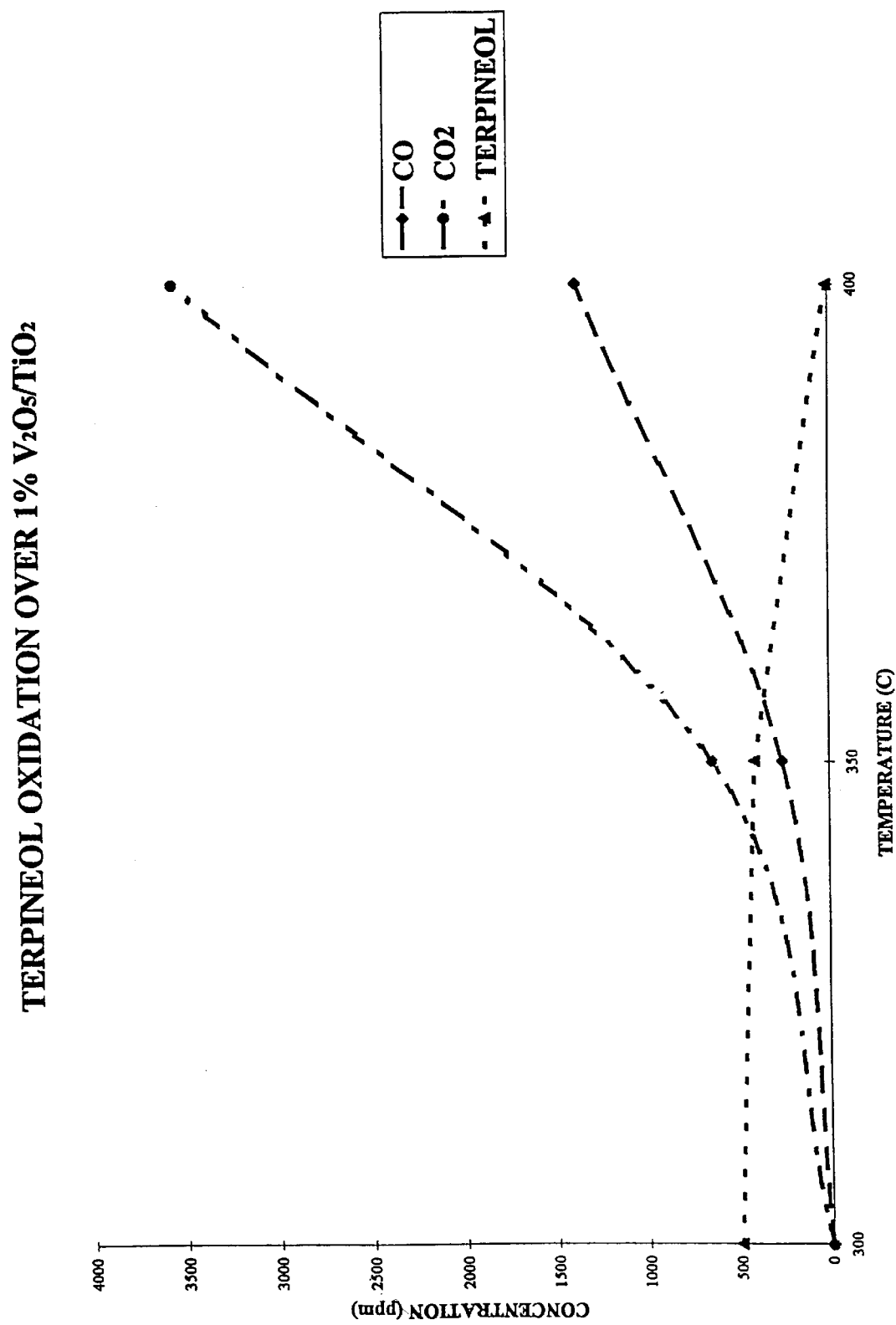
FIG. 11 illustrates the distribution of products produced by oxidizing terpineol over a vanadia on titania catalyst containing about 1% by weight vanadia over the temperature range of 300° to 400° C.

Using substantially the same equipment and procedures as Examples 1 and 2, the impact of the presence of reduced sulfur ($H_2S$) on the partial oxidation of methanol to formaldehyde over a vanadia-titania supported metal oxide catalyst was investigated. A mixture of methanol and hydrogen sulfide, diluted in helium to a concentration of 1200 ppm $CH_3OH$ and 1200 ppm $H_2S$, was contacted with 10 mg of a catalyst comprising about 1% vanadia ($V_2O_5$) on titania ($TiO_2$) in the presence of oxygen and over a wide range of temperatures. The gas stream was passed in contact with the catalyst at a flow rate of 150 ml/min. Conversions were measured by both increasing and decreasing the temperature between 150 and 400° C., and no temperature hysteresis was observed. The reaction products of this reaction, as a function of temperature, are graphically presented in FIG. 7. As illustrated, formaldehyde was found to be the predominant product from methanol oxidation. As the results show, methanol conversion was not affected by the presence of hydrogen sulfide. The reaction products observed were the same as those observed in Example 1, with the exception of $SO_2$ from the oxidation of hydrogen sulfide.

Examples 4–7

Again using the equipment and procedures (e.g., flow rate) of Examples 1 and 2 the behavior of hydrogen sulfide (1050 ppm), acetone (1000 ppm), isopropanol (1000 ppm) and terpineol (500 ppm) over the same catalyst and a similar temperature range were examined. The results are shown, respectively, in FIGS. 8 through 11.

Example 8

Figure 12:
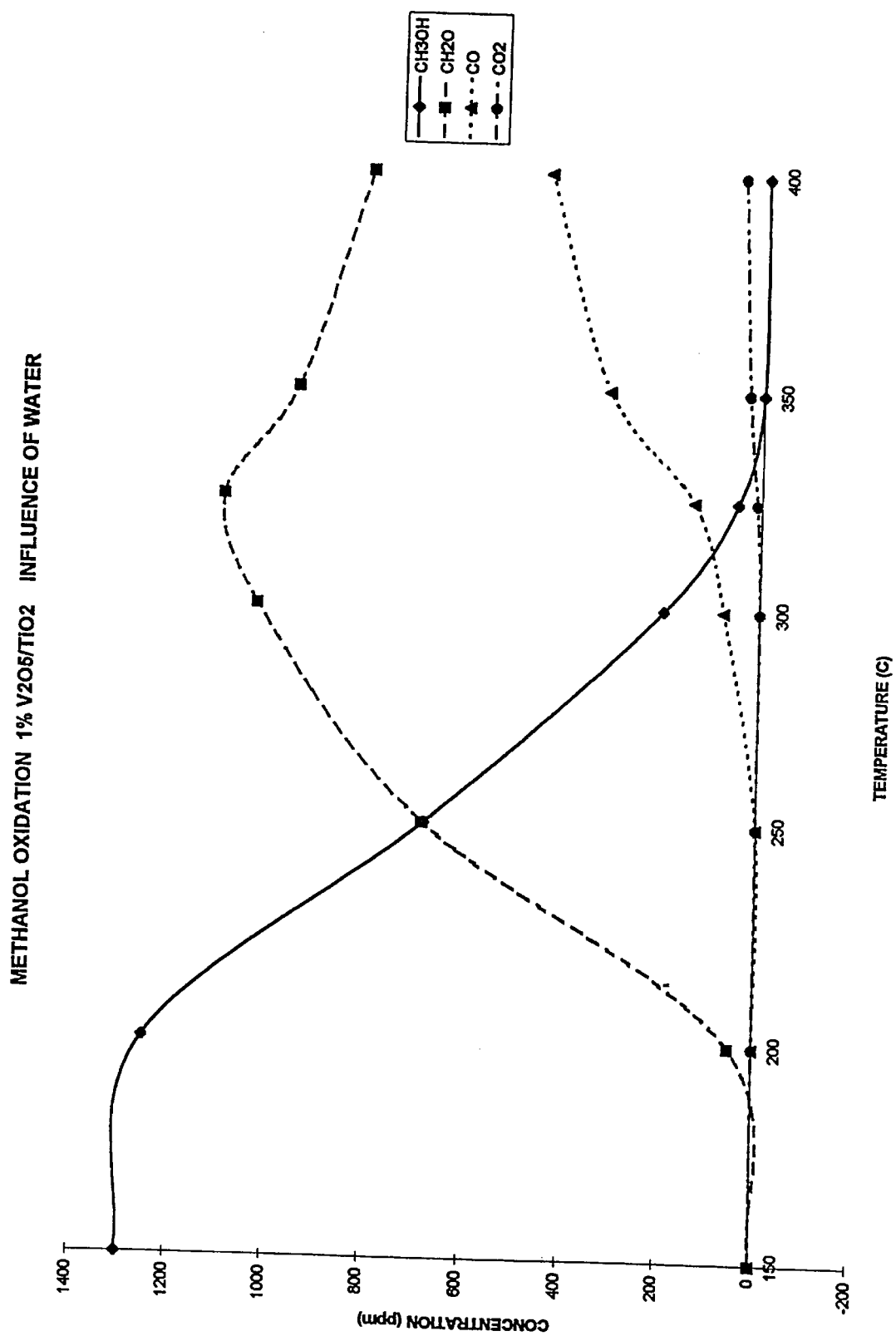
FIG. 12 illustrates the distribution of products produced by oxidizing methanol over a vanadia on titania catalyst containing about 1% by weight vanadia in the presence of air containing 2% water over the temperature range of 150° to 400° C.

In this example the impact of water on the partial oxidation of methanol to formaldehyde was examined using a vanadia on titania catalyst. In particular, using the equipment and procedures of Example 1 and 2, a gas containing 1300 ppm of methanol was contacted with 10 mg of the catalyst in the presence of a stoichiometric excess of air, as the oxygen source, containing 2% water (by volume). The gas stream was passed in contact with the catalyst at a flow rate of 150 ml/min. The results are presented graphically in FIG. 12. The presence of water in the feed stream suppressed the formation of dimethoxymethane as well as the conversion of methanol at a specific temperature.

Example 9

Gases containing methanethiol (1000 ppm), hydrogen sulfide (1050 ppm), dimethyl sulfide (513 ppm) and dimethyl disulfide (490 ppm) were passed at a flow rate of 150 ml/min in contact with 500 mg of a 1% vanadia on titania catalyst at 400° C. in the presence of a stoichiometric excess of oxygen. The products were predominantly a mixture of sulfur dioxide, carbon oxides and water. About 97% of the methanethiol, 99.5% of the hydrogen sulfide, 99% of the dimethyl sulfide and 98% of the dimethyl disulfide were converted on a single pass through the reactor.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention, which is limited only by the appended claims.

What is claimed is:

1. A process for producing formaldehyde from a methanol-containing pulp mill waste gas stream which comprises contacting said methanol-containing waste gas stream with a supported metal oxide catalyst under oxidizing conditions to convert at least a portion of the methanol to formaldehyde, and recovering said formaldehyde from said gas.

2. The process of claim 1 wherein said methanol-containing waste gas is produced from a pulp mill waste condensate stream.

3. The process of claim 1 wherein the supported metal oxide catalyst has a metal oxide overlayer of a metal selected from the group consisting of titanium (Ti), zirconium (Zr), molybdenum (Mo), rhenium (Re), vanadium (V), chromium (Cr), tungsten (W), manganese (Mn), niobium (Nb), tantalum (Ta) and mixtures thereof.

4. The process of claim 3 wherein the supported metal oxide catalyst has a metal oxide support selected from the group consisting of titania, silica, zirconia, alumina, niobia, magnesia, ceria, lanthanum oxide, tin oxide and mixtures thereof.

5. The process of claim 4 wherein the metal oxide overlayer comprises 0.1 to 35 percent by weight of the supported metal oxide catalyst.

6. The process of claim 2 wherein the supported metal oxide catalyst is selected from the group consisting of a vanadia overlayer on a titania support, a molybdenum oxide overlayer on a titania support, a chromium oxide overlayer on a titania support, a rhenium oxide overlayer on a titania support, a vanadia overlayer on a zirconia support, a vanadia overlayer on a niobia support, a vanadia overlayer on an alumina support, a vanadia overlayer on a silica support, a tungsten oxide overlayer on a silica support, a niobia overlayer on a silica support, and a titania overlayer on a silica support.

7. The process of claim 6 wherein the metal oxide overlayer comprises 0.1 to 35 percent by weight of the supported metal oxide catalyst.

8. The process of claim 7 wherein the supported metal oxide catalyst comprises a vanadia overlayer, in an amount of 1 to 10% by weight of said supported metal catalyst, on a titania support.

9. The process of claim 1 wherein said contacting is conducted at a temperature between 200° and 700° C.

10. The process of claim 9 wherein said contacting is conducted at a temperature between 325° and 500° C.

11. The process of claim 10 wherein said methanol-containing waste gas stream is contacted with said catalyst such that between $10^2$ and $10^5$ cubic centimeters of methanol contacts a gram of catalyst per minute.

12. The process of claim 1 wherein between 0.1 and $10^4$ cubic centimeters of methanol contact a gram of catalyst per minute.

13. A process for oxidizing a pulp mill waste gas stream containing oxidizable carbon-containing and sulfur-containing constituents which comprises, contacting said gas with a supported metal oxide catalyst under oxidizing conditions to convert the carbon-containing constituents to carbon oxides and the sulfur-containing constituents to sulfur oxides.

14. The process of claim 13 wherein said waste gas stream is produced from a pulp mill condensate.

15. The process of claim 14 wherein the supported metal oxide catalyst has a metal oxide overlayer of a metal selected from the group consisting of titanium (Ti), zirconium (Zr), molybdenum (Mo), rhenium (Re), vanadium (V), chromium (Cr), tungsten (W), manganese (Mn), niobium (Nb), tantalum (Ta) and mixtures thereof.

16. The process of claim 15 wherein the supported metal oxide catalyst has a metal oxide support selected from the group consisting of titania, silica, zirconia, alumina, niobia, magnesia, ceria, lanthanum oxide, tin oxide and mixtures thereof.

17. The process of claim 16 wherein the metal oxide overlayer comprises 0.1 to 35 percent by weight of the supported metal oxide catalyst.

18. The process of claim 17 wherein the supported metal oxide catalyst is selected from the group consisting of a vanadia overlayer on a titania support, a molybdenum oxide overlayer on a titania support, a chromium oxide overlayer on a titania support, a rhenium oxide overlayer on a titania support, a vanadia overlayer on a zirconia support, a vanadia overlayer on a niobia support, a vanadia overlayer on an alumina support, a vanadia overlayer on a silica support, a tungsten oxide overlayer on a silica support, a niobia overlayer on a silica support, and a titania overlayer on a silica support.

19. The process of claim 18 wherein the metal oxide overlayer comprises 0.1 to 35 percent by weight of the supported metal oxide catalyst.

20. The process of claim 19 wherein the supported metal oxide catalyst comprises a vanadia overlayer, in an amount of 1 to 10% by weight of said supported metal catalyst, on a titania support.

21. The process of claim 20 wherein said contacting is conducted at a temperature between 200° and 700° C.

* * * * *